United States Patent
Hsu et al.

(10) Patent No.: US 10,028,758 B2
(45) Date of Patent: Jul. 24, 2018

(54) SHOCKWAVE PROBE TRANSDUCER STRUCTURE

(71) Applicant: Lite-Med Inc., Taipei (TW)

(72) Inventors: Walt Hsu, Taipei (TW); Chia-Chi Lin, Taipei (TW)

(73) Assignee: LITE-MED INC., Taipei (TW)

( * ) Notice: Subject to any disclaimer, the term of this patent is extended or adjusted under 35 U.S.C. 154(b) by 295 days.

(21) Appl. No.: 14/956,451

(22) Filed: Dec. 2, 2015

(65) Prior Publication Data

US 2017/0065289 A1    Mar. 9, 2017

(30) Foreign Application Priority Data

Sep. 4, 2015 (TW) .............................. 104129422 A

(51) Int. Cl.
  *A61B 17/22* (2006.01)
  *A61B 17/225* (2006.01)
  *A61B 17/00* (2006.01)

(52) U.S. Cl.
  CPC .... *A61B 17/22004* (2013.01); *A61B 17/2251* (2013.01); *A61B 17/225* (2013.01); *A61B 2017/00473* (2013.01); *A61B 2017/00477* (2013.01); *A61B 2017/22027* (2013.01)

(58) Field of Classification Search
  CPC ............ A61B 17/22004; A61B 17/225; A61B 17/2251; A61B 2017/00473; A61B 2017/00477; A61B 2017/22027
  See application file for complete search history.

(56) References Cited

U.S. PATENT DOCUMENTS

| | | | | |
|---|---|---|---|---|
| 4,905,675 A | * | 3/1990 | Oppelt | G10K 9/12 601/4 |
| 9,555,267 B2 | * | 1/2017 | Ein-Gal | A61N 7/00 |
| 2006/0064082 A1 | * | 3/2006 | Bonutti | A61N 7/00 606/32 |

* cited by examiner

*Primary Examiner* — Ruth S Smith
(74) *Attorney, Agent, or Firm* — Juan Carlos A. Marquez; Marquez IP Law Office, PLLC

(57) ABSTRACT

A shockwave probe transducer structure includes a shock cup, a magnetic disc and a focusing module. The focusing module includes a circular cover and a focusing member installed between the circular cover and the shock cup. The focusing member is consisted of a focusing bag or a lens and a focusing bag closely coupled to each other. The focal point of the shockwave of the shockwave probe transducer structure can be changed by simply changing the focusing module installed at the front of the shockwave probe transducer structure, so as to overcome the problems of complicated changing procedure and possible water leakage and avoid the risk of damaging an expensive shockwave system or jeopardizing the safety of people.

12 Claims, 7 Drawing Sheets

SHOCKWAVE PROBE TRANSDUCER STRUCTURE

BACKGROUND OF THE INVENTION

1. Technical Field

The present invention relates to a probe transducer structure, and more particularly to a shockwave probe transducer structure capable of achieving for shockwave lithotripsy.

2. Description of Related Art

Ultrasonic or shockwave detection refers to "the detection of flaws in a human body or an object by low-energy high-frequency ultrasound". The high penetration of the ultrasound or shockwave can detect a very thick object. In addition, the shockwave detection using ultrasounds has no harm on human body and is capable of determine the internal flaws of the object immediately, and this is the major advantage of the shockwave detection.

The general ultrasonic or shockwave detection adopts a frequency from 1 MHz to 25 MHz, and basic equipment requires an electronic signal generator or uses a transducer (or a shockwave probe, a transducer of probe or a search unit) to emit ultrasound or shockwave. The ultrasound or shockwave is sent into a human body or an object by couplings. The ultrasound or shockwave in the human body or object may be deteriorated to a certain extent, so that when the ultrasound or shockwave is transmitted to the an interface of a substance, the ultrasound or shockwave is reflected or transmitted, and the reflected or transmitted signal is detected and analyzed to determine a flaw of the human body or object and the position of the flaw.

In the ultrasonic or shockwave detection, it is necessary to change the whole set of the shockwave probe in order to change the focal point of a conventional shockwave probe, and thus requiring a complicated changing procedure and taking much effort and precious treatment time. Since most ultrasonic or shockwave systems are connected to a water filling structure and a complicated and high-pressure pipeline, water will leak easily or even damage the expensive ultrasonic or shockwave system will be damaged if the whole set of the ultrasonic probe is changed.

In view of the aforementioned problems, it is an urgent and important subject for related manufacturers to design and develop a shockwave probe transducer structure having the features of changing the focal point of the ultrasound or shockwave by a simple procedure and preventing water leakage to benefit medical ultrasonic or shockwave equipment users.

SUMMARY OF THE INVENTION

The present invention relates to a shockwave probe transducer structure comprising: a shock cup; a magnetic disc; and a focusing module, wherein the focusing module includes a circular cover and a focusing member fixed and installed between the circular cover and the shock cup, and the focusing member is consisted of a focusing bag, or a lens and a focusing bag closely coupled to one another. With the implementation of the present invention, the focal point of the shockwave of the shockwave probe transducer structure can be changed by simply changing the focusing module installed at the front of the shockwave probe transducer structure, so as to overcome the problems of complicated changing procedure and possible water leakage and avoid the risk of damaging an expensive shockwave system or jeopardizing the safety of people.

The present invention provides a shockwave probe transducer structure, comprising: a shock cup, including a housing, a first opening, a second opening configured to be opposite to the first opening, and a fixed disc capable of detachably sealing the second opening; a magnetic disc, installed on the fixed disc in the housing, and having a shock plate fixed onto a surface of the magnetic disc proximate to the first opening; and a focusing module, detachably sealed and fixed onto the first opening, and a gap filled up with a medium being formed between the focusing module and the magnetic disc, and the focusing module including a circular cover and a focusing member installed between the circular cover and the shock cup, and a portion of the focusing member being extended and protruded out from the circular cover.

Implementation of the present invention at least involves the following inventive steps:

1. The modularization of the shockwave probe transducer structure simplifies the complexity of changing the focal point of the shockwave significantly;

2. The shockwave probe transducer structure is capable of avoiding water leakage to prevent the expensive ultrasonic or shockwave system from being damaged by water leakage; and 3. The shockwave probe transducer structure is capable of avoiding jeopardizing the safety of people when changing the focal point of the shockwave.

The features and advantages of the present invention are detailed hereinafter with reference to the preferred embodiments. The detailed description is intended to enable a person skilled in the art to gain insight into the technical contents disclosed herein and implement the present invention accordingly. In particular, a person skilled in the art can easily understand the objects and advantages of the present invention by referring to the disclosure of the specification, the claims, and the accompanying drawings.

BRIEF DESCRIPTION OF THE SEVERAL VIEWS OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE EMBODIMENTS OF THE INVENTION

Figure 1:
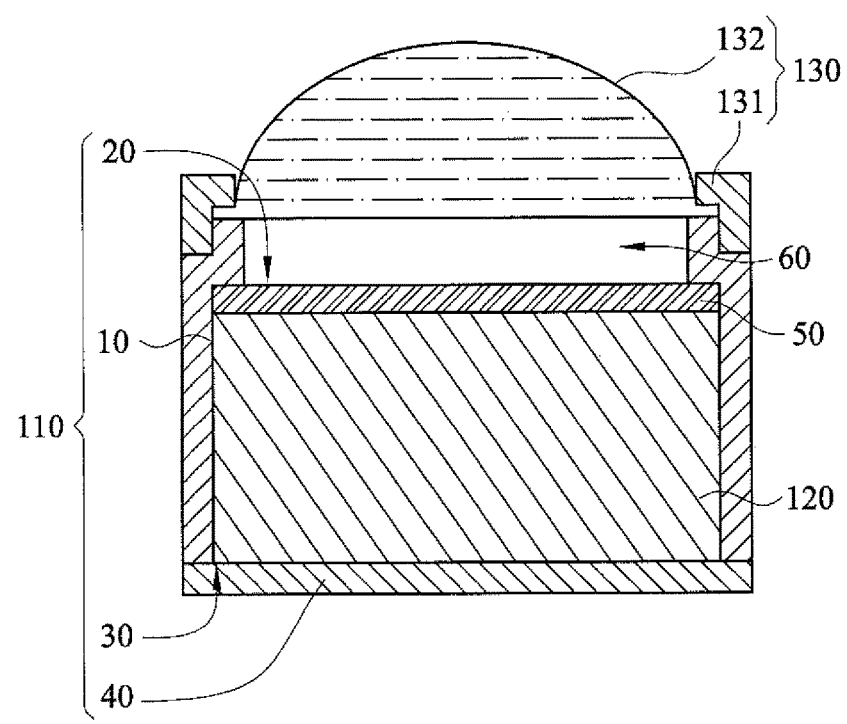
FIG. 1 is a cross-sectional side view of a shockwave probe transducer structure of a preferred embodiment of the present invention.

With reference to FIG. 1 for a shockwave probe transducer structure 100 in accordance with a preferred embodiment of the present invention, the shockwave probe transducer structure 100 comprises a shock cup 110, a magnetic disc 120, and a focusing module 130. The focusing module 130 further comprises a circular cover 131 and a focusing member 132 fixed and installed between the circular cover 131 and the shock cup 110.

Figure 2:
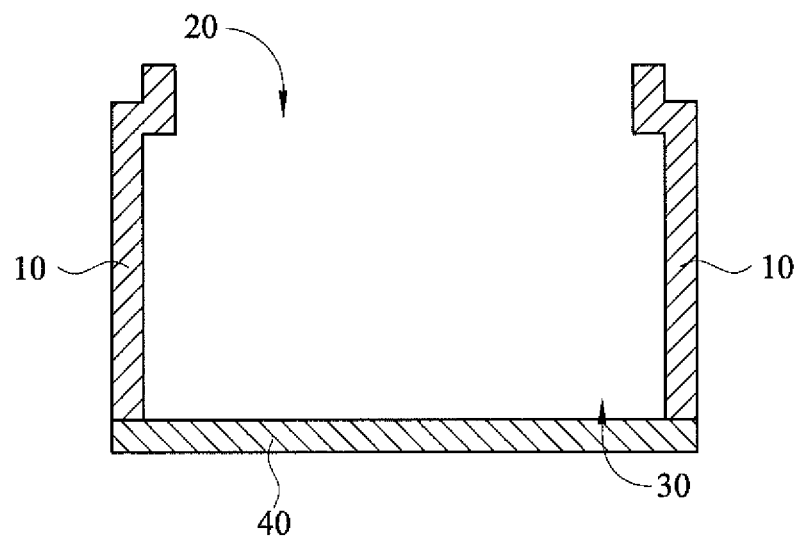
FIG. 2 is a cross-sectional side view of a shock cup of a preferred embodiment of the present invention.

In FIGS. 1 and 2, the shock cup 110 comprises a housing 10, a first opening 20, a second opening 30 configured to be opposite to the first opening 20, and a fixed disc 40 capable of detachably sealing the second opening 30, wherein the shock cup 110 is made of a watertight, airtight and durable material, but the invention is not limited to such material only.

In FIG. 1, the magnetic disc 120 is installed on the fixed disc 40 in the housing 10, and a shock plate 50 is installed onto a surface of the magnetic disc 120 proximate to the first opening 20. If the shock plate 50 is electrically connected externally to the magnetic disc 120, the shock plate 50 will be attracted or repelled according to the changing frequency of the input signal by the change of the magnetism and the direction of the magnetic force generated by the input signal, so that the shock plate 50 will generate a shockwave 200 (see FIGS. 4B and 5B).

Figure 3:
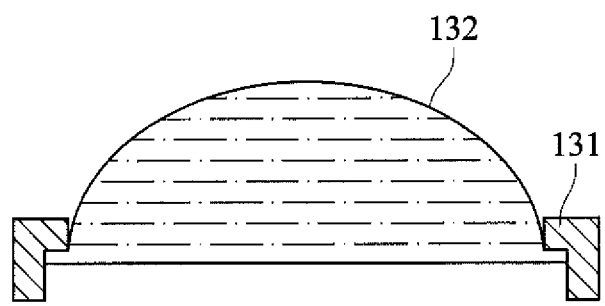
FIG. 3 is a cross-sectional side view of a focusing module of a preferred embodiment of the present invention.

In FIGS. 1 and 3, the focusing module 130 is detachably sealed onto the first opening 20, and a gap 60 filled up with a medium is formed between the focusing module 130 and the shock plate 50. In addition, the focusing module 130 further comprises a circular cover 131 and a focusing member 132 fixed and installed between the circular cover 131 and the shock cup 110, and a portion of the focusing member 132 is extended and protruded out from the circular cover 131.

The medium filled up in the gap 60 between the focusing module 130 and the shock plate 50 may be water or a shockwave transmitting medium mainly used for generating the shockwave 200 by the shock plate 50, and the medium filled up in the gap 60 between the focusing module 130 and the shock plate 50 is transmitted to the focusing module 130, and then focused by the focusing module 130 and emitted to the outside.

Figure 4A:
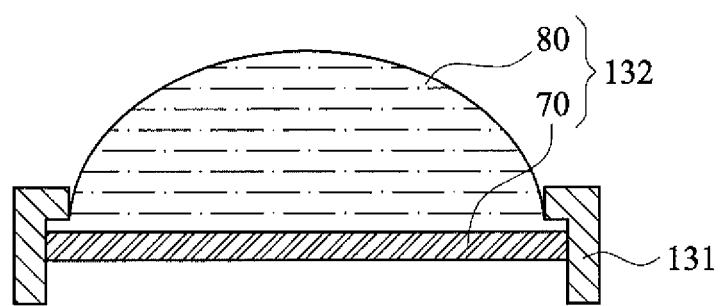
FIG. 4A is a cross-sectional side view of another focusing module of a preferred embodiment of the present invention.

In FIG. 4A, the focusing member 132 includes a lens 70 and a focusing bag 80 closely coupled to each other, and the lens 70 is disposed between the focusing bag 80 and the shock plate 50. The lens 70 is made of a material such as a shockwave transmitting medium, so that the lens 70 has the function of transmitting and focusing shockwave.

The aforementioned shockwave transmitting medium is preferably silicone for convenient access and use, regardless of its being used for making the lens 70 or filled up into the gap 60 between the focusing module 130 and the shock plate 50.

Figure 4B:
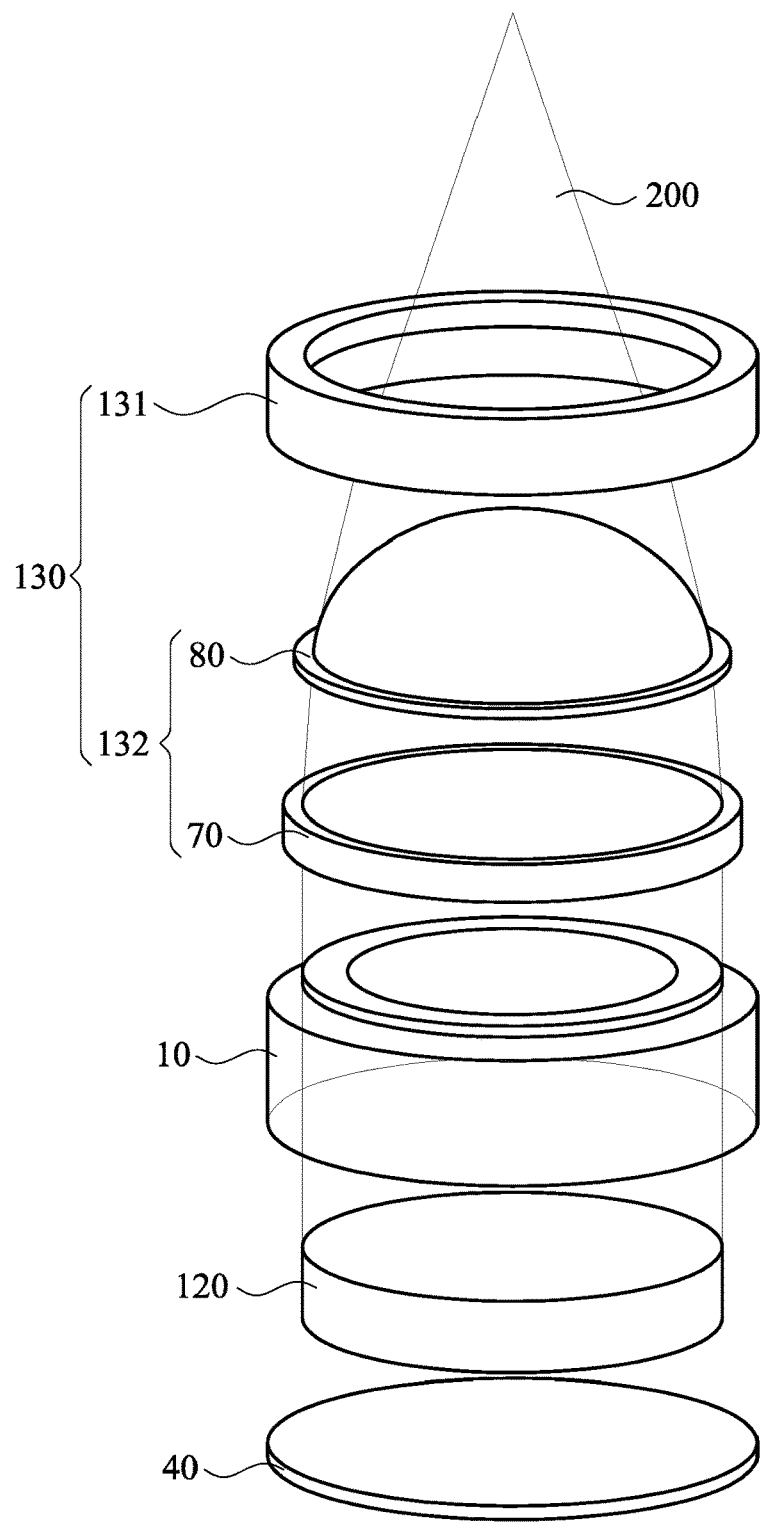
FIG. 4B is an exploded view of a shockwave probe transducer structure of a focusing module for generating shockwaves in accordance with the preferred embodiment as depicted in 4A.

With reference to FIG. 4B for an exploded view of a shockwave probe transducer structure capable of generating a shockwave 200 in accordance with a preferred embodiment of the present invention, the focusing member 132 includes a lens 70 and a focusing module 130 of a focusing bag 80.

Figure 5A:
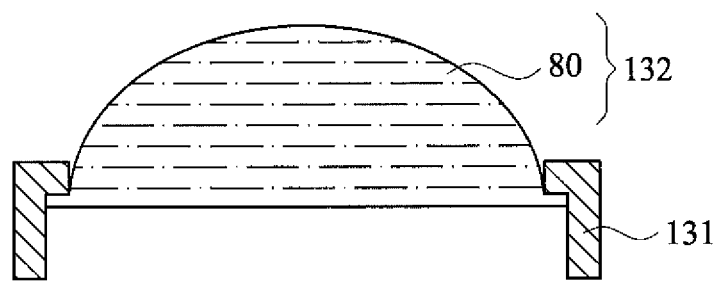
FIG. 5A is a cross-sectional side view of another focusing module of a preferred embodiment of the present invention.

In FIG. 5A, the focusing member 132 is consisted of a focusing bag 80 only. In FIG. 4A~4B or 5A~5B, the focusing bag 80 is consisted of a water bag, a silicone bag, or a shockwave transmitter capable of focusing the shockwave.

In FIGS. 4A~5B, if the focusing bag 80 is a silicone bag, the focusing bag 80 may be made of silicone and integrally formed.

Figure 5B:
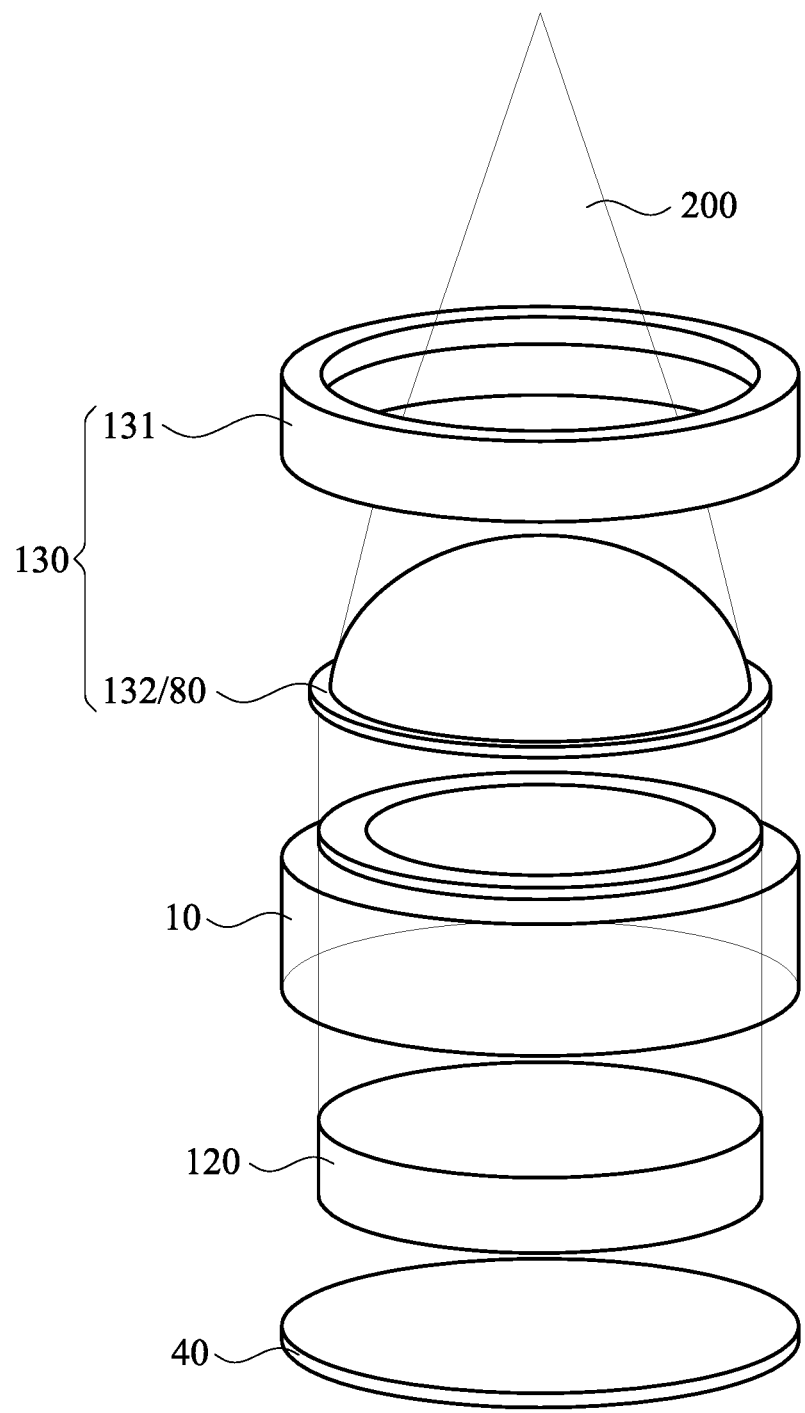
FIG. 5B is an exploded view of a shockwave probe transducer structure of a focusing module for generating shockwaves in accordance with the preferred embodiment as depicted in 5A.

With reference to FIG. 5B for an exploded view of a shockwave probe transducer structure using the focusing member 132 as the focusing bag 80 and its generated shockwave 200, the magnetic disc 120 attracts or repels the shock plate 50 to generate the shockwave 200, and the shockwave 200 is transmitted to the focusing module 130 by the medium filled up in the gap 60 between the focusing module 130 and the shock plate 50, and focused and emitted to the outside by the focusing module 130 which just has the focusing bag 80.

Figure 6:
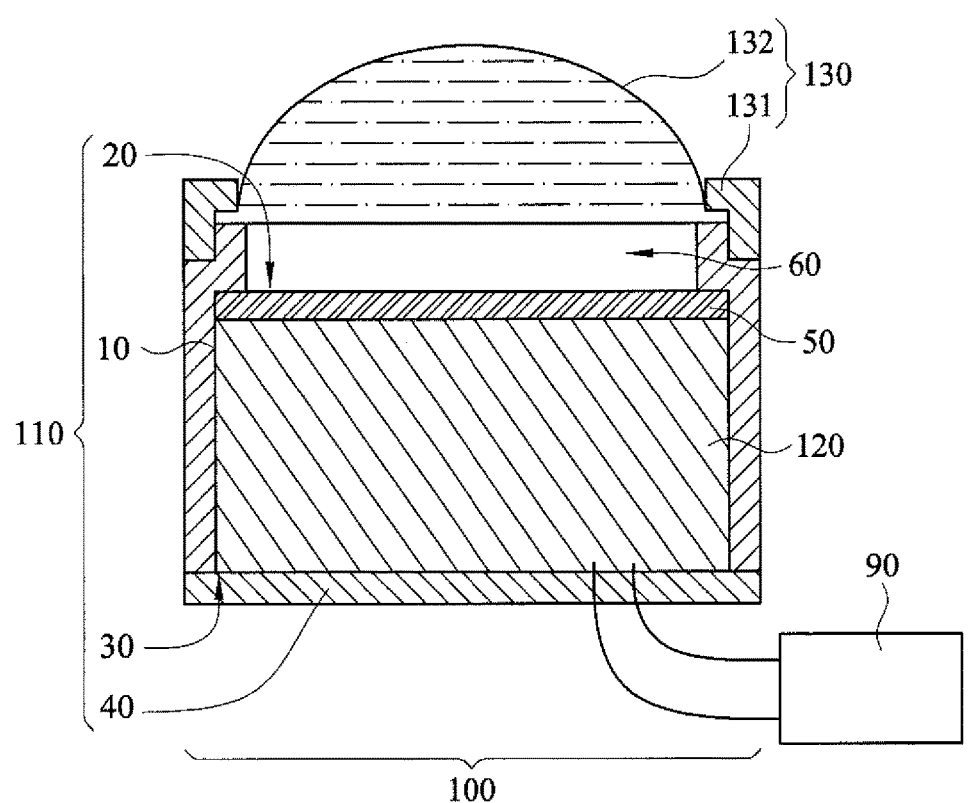
FIG. 6 is a cross-sectional side view of a shockwave probe transducer structure combined with a control circuit in accordance with a preferred embodiment of the present invention.

In FIG. 6, the shockwave probe transducer structure 100 is further combined with a control circuit 90. The control circuit 90 is provided for outputting a voltage waveform to the magnetic disc 120 to control the magnetic wave generated by the magnetic disc 120, so that the shock plate 50 generates a shockwave 200.

Therefore, the amplitude or frequency of the voltage waveform outputted to the magnetic disc 120 by the control circuit 90 may be selected to adjust and control the magnitude or frequency of the shockwave 200 generated by the shockwave probe transducer structure.

The focusing member 132 just having the lens 70 and the focusing bag 80 or the focusing member 132 just having the focusing bag 80 is provided for focusing and emitting the shockwave 200 to the outside. We simply need to change the focusing module 130 including the circular cover 131 and the focusing member 132 in order to change the focal point of the shockwave 200.

The modularization of the shockwave probe transducer structure simplifies the procedure of changing the focal point of the shockwave 200, and the present invention further avoids the situation of a water leakage to prevent damaging the expensive ultrasonic system or jeopardizing the safety of people.

The shockwave 200 as described in the foregoing preferred embodiments may be an ultrasonic wave, a sonic wave or any shockwave 200 other than the ultrasonic wave and applied in medical treatment systems.

The embodiments described above are intended only to demonstrate the technical concept and features of the present invention so as to enable a person skilled in the art to understand and implement the contents disclosed herein. It is understood that the disclosed embodiments are not to limit the scope of the present invention. Therefore, all equivalent changes or modifications based on the concept of the present invention should be encompassed by the appended claims.

What is claimed is:

1. A shockwave probe transducer structure, comprising:
   a cup, including a housing, a first opening, a second opening configured to be opposite to the first opening, and a fixed disc connected to the second opening to detachably seal the second opening;
   a magnetic disc, attached to the fixed disc in the housing, and having a plate fixed onto a surface of the magnetic disc proximate to the first opening; and
   a focusing module, detachably sealed and fixed onto the first opening, and a gap filled up with a medium between the focusing module and the magnetic disc, and the focusing module including a circular cover and a focusing bag between the circular cover and the cup, and a portion of the focusing bag being extended and protruded out from the circular cover.

2. The shockwave probe transducer structure according to claim 1, wherein the medium is water or a shockwave transmitting medium.

3. The shockwave probe transducer structure according to claim 1, wherein the focusing module further includes a lens closely coupled with the focusing bag.

4. The shockwave probe transducer structure according to claim 3, wherein the lens includes a shockwave transmitting medium.

5. The shockwave probe transducer structure according to claim 4, wherein the shockwave transmitting medium is silicone.

6. The shockwave probe transducer structure according to claim 3, wherein the focusing bag is a water bag.

7. The shockwave probe transducer structure according to claim 3, wherein the focusing bag is a silicone bag.

8. The shockwave probe transducer structure according to claim 3, wherein the focusing bag includes a shockwave transmitter capable of focusing a shockwave.

9. The shockwave probe transducer structure according to claim 1, wherein the focusing bag is a water bag.

10. The shockwave probe transducer structure according to claim 1, wherein the focusing bag is a silicone bag.

11. The shockwave probe transducer structure according to claim 1, wherein the focusing bag includes a shockwave transmitter capable of focusing a shockwave.

12. The shockwave probe transducer structure according to claim 1, further comprising a control circuit operatively connected to the shockwave probe transducer structure for outputting a voltage waveform to the magnetic disc and controlling the magnetic disc to generate a magnetic wave, so that the plate generates a shockwave.

* * * * *